(12) United States Patent
Floyd

(10) Patent No.: US 6,598,477 B2
(45) Date of Patent: Jul. 29, 2003

(54) METHOD OF EVALUATING LOGS TO PREDICT WARP PROPENSITY OF LUMBER SAWN FROM THE LOGS

(75) Inventor: Stanley L. Floyd, Enumclaw, WA (US)

(73) Assignee: Weyerhaeuser Company, Federal Way, WA (US)

( * ) Notice: Subject to any disclaimer, the term of this patent is extended or adjusted under 35 U.S.C. 154(b) by 66 days.

(21) Appl. No.: 10/002,427

(22) Filed: Oct. 31, 2001

(65) Prior Publication Data

US 2003/0079544 A1 May 1, 2003

(51) Int. Cl.[7] .................. G01N 33/46; G01R 27/26; G06F 7/60
(52) U.S. Cl. ................. 73/597; 73/602; 73/432.1; 144/357; 83/73; 83/361; 83/365; 83/371
(58) Field of Search ............ 73/597, 601, 602, 73/624, 627, 628, 73, 75, 159, 160, 432.1; 356/364, 371, 376, 383, 384, 445–448, 237, 239; 250/330, 338.1, 341.4, 340, 341.6, 341.8, 358.1, 359.1, 360.1; 144/356, 357, 380, 360; 702/35, 38–40, 81, 179–180, 181, 189, 196, 126, 134, 135, 136, 155; 83/75.5, 425.2, 69–73, 360–361, 365, 370, 371

(56) References Cited

U.S. PATENT DOCUMENTS

| | | | | |
|---|---|---|---|---|
| 4,852,029 A | * | 7/1989 | Pope et al. ............ | 702/41 |
| 5,579,671 A | * | 12/1996 | Bowlin ............ | 83/75.5 |
| 5,960,104 A | * | 9/1999 | Conners et al. ........ | 382/141 |
| 6,026,689 A | | 2/2000 | Snyder et al. .......... | 73/602 |
| 6,293,152 B1 | * | 9/2001 | Stanish et al. .......... | 73/597 |
| 6,305,224 B1 | * | 10/2001 | Stanish et al. .......... | 73/597 |
| 6,308,571 B1 | * | 10/2001 | Stanish et al. .......... | 73/597 |
| 6,463,402 B1 | * | 10/2002 | Bennett et al. ......... | 703/2 |
| 2003/0029518 A1 | * | 2/2003 | Starr .................. | 144/340 |
| 2003/0029519 A1 | * | 2/2003 | Starr .................. | 144/340 |

FOREIGN PATENT DOCUMENTS

| | | | | |
|---|---|---|---|---|
| GB | 1244699 | 9/1971 | ......... | G01N/33/46 |
| WO | WO 0011467 | 3/2000 | ......... | G01N/33/46 |
| WO | WO 00/12230 | 3/2000 | ......... | B07C/5/14 |
| WO | WO 00/36413 | 6/2000 | ......... | G01N/33/46 |
| WO | WO 01/09603 | 2/2001 | ......... | G01N/33/46 |

OTHER PUBLICATIONS

Wagner, F.G. and F. W. Taylor. Inpact of log sweep on warp in southern pine structural lumber, *Forest Products Journal*, 45(2): 59–62 (1995).

* cited by examiner

*Primary Examiner*—Helen Kwok
*Assistant Examiner*—Rose M. Miller

(57) ABSTRACT

A method of predicting warp of lumber that might be sawn from any given log is disclosed. The method involves measurement of stress wave velocity in the tree stem. A scan is then made to define the exterior geometric configuration of the log. In particular, measurements relating to lack of longitudinal axis linearity (sweep) or irregularity of cross sections of the log are important. Stress wave values and selected geometric parameters are entered into a multivariate regression equation to predict warp propensity of lumber that might be sawn from the log. The equations are originally derived by examination of a representative population of logs of the particular species and locale and measurement of warp in lumber sawn from the logs. Logs determined to produce warp prone lumber can be isolated and used to produce other products such as timbers or plywood where warp is not as critical.

28 Claims, 12 Drawing Sheets

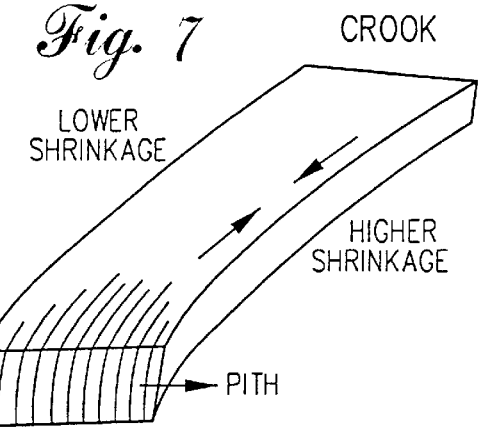
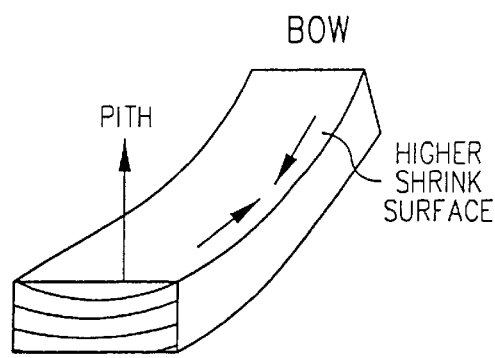
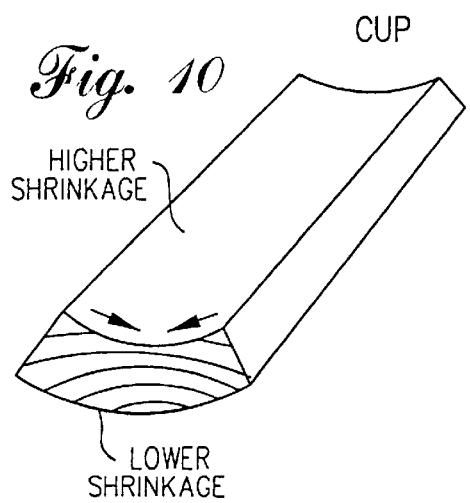
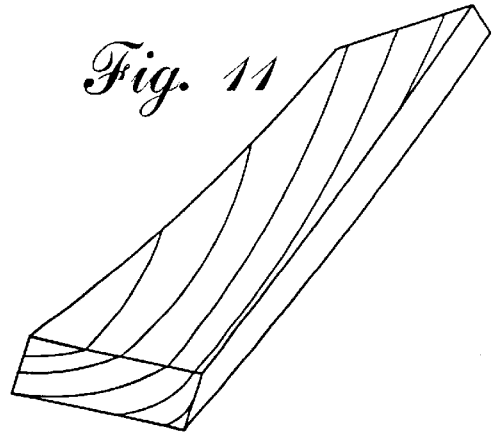
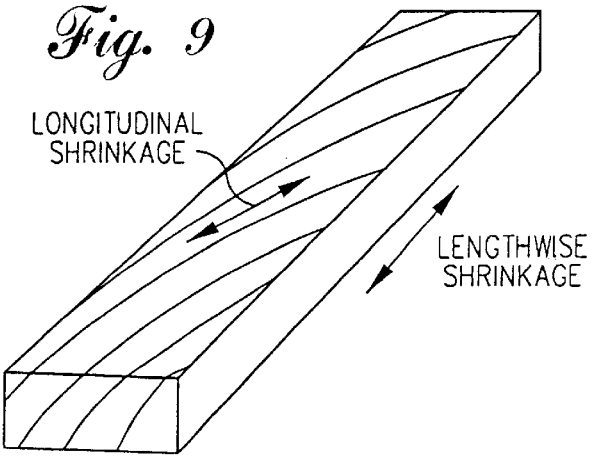

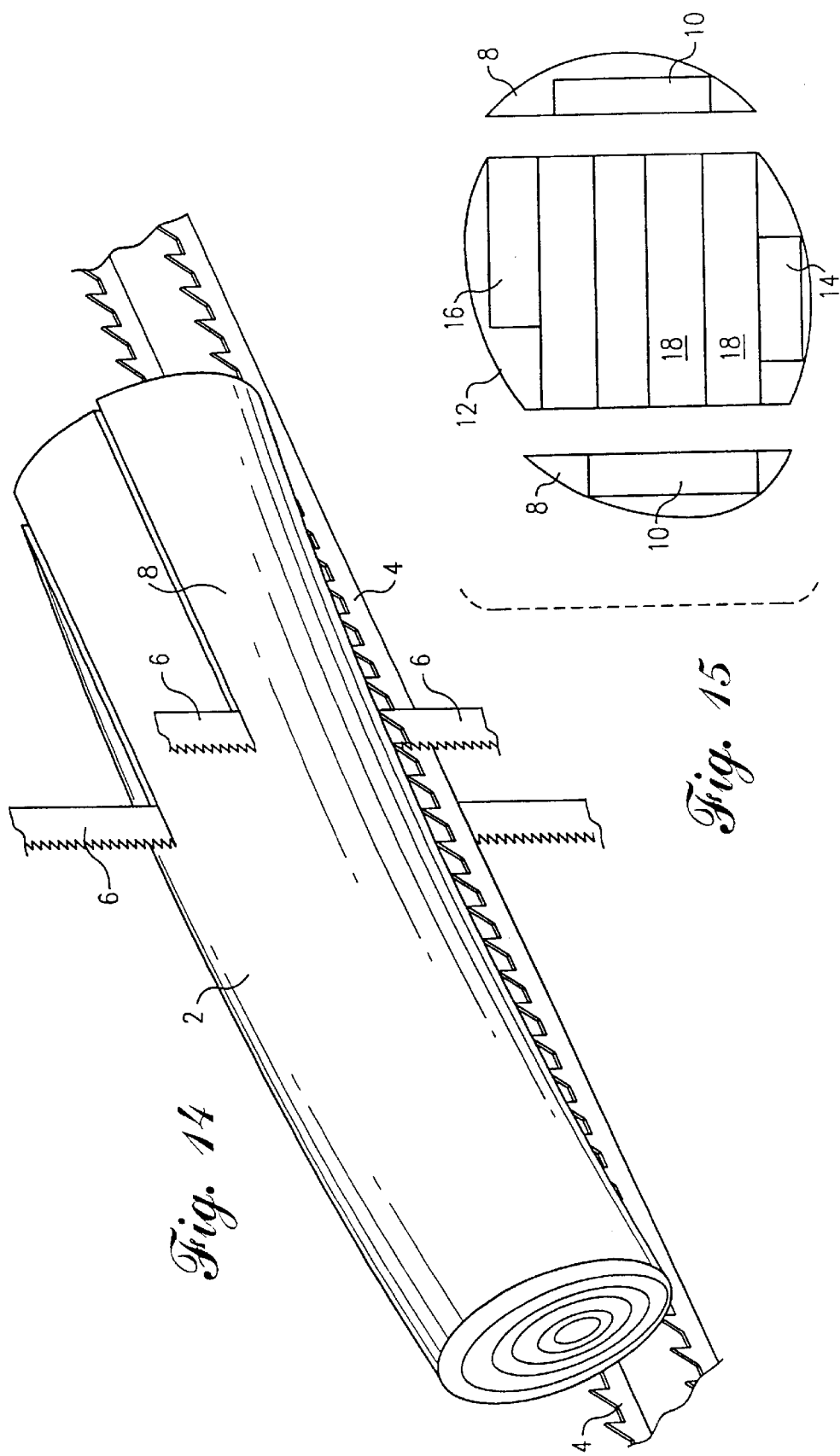

METHOD OF EVALUATING LOGS TO PREDICT WARP PROPENSITY OF LUMBER SAWN FROM THE LOGS

The present invention is directed to a method for evaluating logs to predict warping tendency of lumber that might be cut from a given log. The method can be used in a sorting yard, on-line in a sawmill, or at other locations along the route from forest to mill. It enables decisions whether a log should be directed to a sawmill for lumber manufacture or for other applications such as timbers, plywood, or pulp chips. The method enables a sawyer to make real time decisions as to how a log should be cut to obtain maximum product utility.

BACKGROUND OF THE INVENTION

The majority of the available old growth softwood forests in the world have now been harvested. This wood has now been replaced in many areas of the world by trees grown on intensively managed plantations or "tree farms". Over the years nurseries producing seed for plantation trees have used intensive genetic selection to improve such heritable traits as rapid growth, straightness of stem, reduced limb diameter, and other desirable characteristics. Most growth cycles now include one or more fertilizations. Plantation trees are also usually thinned and may be pruned one or more times. While plantations now provide a dependable supply of wood for lumber and pulp, the transition from old growth to plantation wood has seen a significant change in size and characteristics of the wood supplied to the mills. Depending on the species and growth locale, plantation trees for saw logs are usually harvested on a 20–50 year growth cycle. The various pine species are usually harvested 20–30 years after planting and typically produce logs having a butt diameter about 30–60 cm in diameter.

It is the nature of most conifer species to produce wood having so-called juvenile characteristics during the first 10–15 years of their growth. This juvenile wood is characterized by thinner cell (tracheid) walls and a higher microfibril angle in the tracheid walls. One characteristic of juvenile wood is reduced density. Another, attributed to the greater microfibril angle, is greater longitudinal shrinkage on drying. Density increases as wood is laid down at greater distances from the pith and the microfibril angle decreases until wood laid down after about 12–15 years growth has acquired "adult" properties. Under normal conditions, density and microfibril angle then remain essentially constant during the remaining years of the tree's growth. This difference in properties radially across the logs can affect the strength and other properties of lumber sawn from the trees. Density is known to correlate directly with modulus of elasticity. Further, the difference in longitudinal shrinkage from pith to outer wood can be responsible for warp of lumber produced from the logs, particularly the defects known as bow and crook.

Various means have been proposed to overcome the above problems. For example, U.S. Pat. No. 6,001,452 to Bassett et al. shows a composite lumber product in which the denser wood from the outer portions of the tree is selectively located in a composite lumber product to improve bending strength. Similarly, published PCT application WO 00/12230 to Stanish et al. describes a method of predicting warp potential by estimating lengthwise shrinkage rates and measuring grain angle of lumber.

Snyder et al., in U.S. Pat. No. 6,026,689, describe a method of estimating modulus of elasticity of wood (MOE) in a log by impacting the log with a pneumatic hammer and measuring velocity of the resulting stress wave. Related technology is described in PCT Applications WO 00/11467 and WO 01/09603 and British Patent 1,244,699. In general, low stress wave velocity correlates with lower modulus wood. Technology of this general type is used with the present invention.

The method described by Stanish et al. is more applicable to cut lumber than to raw logs. It would be extremely useful if warp propensity could be reliably determined earlier in the process, such as in the sorting yard or even with standing trees, so that logs that would produce warp prone lumber might be directed to other products. Examples could be solid sawn timbers or veneers for plywood where potential dimensional instability poses much less of a problem. Alternatively, other uses such as particle, flake, or oriented strand boards or chips for wood pulp would be possible.

In a study of 75 small pine logs, F. G. Wagner and F. W. Taylor suggest a possible relationship between log sweep with bow or crook of finished lumber (Impact of log sweep on warp in southern pine structural lumber, *Forest Products Journal*, 45(2): 59–62 (1995)).

The present invention is directed to a procedure that makes a highly predictable early warp propensity evaluation of raw logs both possible and fully compatible with operations in the forest, at a sort yard, or in an integrated sawmill.

SUMMARY OF THE INVENTION

The present invention is a method that enables prediction, before the log is milled, of crook and bow that might occur in lumber sawn from a given log. The method includes determination of stress wave velocity in the log by known methods. The method further includes determination of the external geometric configuration of the log which may be done by known scanning methods. Data from these two determinations are then included in a multivariate regression equation that can predict with considerable accuracy the warp tendency of lumber that might be milled from the log. The word "log" should be read to include the stem of standing trees, felled and limbed trees, and felled trees cut into appropriate lengths for processing in a sawmill. In most environments the necessary stress wave and geometric data can be determined on a real time basis before the log is sawn. Stress wave velocity can be programmed into the existing computers associated with log geometry scanners to determine what type of product should be produced from the log. If a high tendency for warp is indicated, the log might be sawn into timbers rather than dimension lumber. Alternatively, it could be directed to production of plywood, wood composites, or chips for pulp manufacture.

Log scanners are available from a number of manufacturers. These are in common use in sawmills and plywood mills. Among other benefits, they can determine the best orientation of the log as it is presented to the primary breakdown saws. Scanners also typically determine optimum settings for primary breakdown and secondary processing saws in order to obtain maximum product value. In the case of plywood, scanners determine the optimum centers for chucking the lathe block.

While there are differences in method of operation and data determined, most log scanners will make a multiplicity of circumferential scans along the length of the log to determine such properties as large and small end diameters, cross sectional shape, and sweep. Sweep is a departure from longitudinal axis linearity in one or more planes. These scans may determine location of a hundred or more points at each of successive log circumferences to determine cross sectional configurations and position them orthogonal to a longitudinal reference line generally parallel to the log being measured. The circumferential configurations are indicative of the log cross section and their displacement from the reference line at the scan location. Successive scans may be from about 1–30 cm apart. These geometric measurements may be digitized and define the outer configuration of the log. The resulting data can be readily manipulated by an associated computer to automatically program downstream manufacturing parameters.

Stress wave velocity analysis is also now frequently used for estimation of thestiffness or modulus of elasticity of logs before lumber manufacture. Various types of apparatus are now commercially available for this measurement. Most will use one or more sensors contacting the log to measure the time of travel of a sound wave produced by a hammer or other device impacting the log. Stress wave time may be determined over the full length of the log or some incremental portion. It can be measured on felled logs or standing trees.

Stress wave velocity has been used in an attempt to predict warp tendency of lumber. However, the correlation has generally been so poor as to be of minimum value. The present inventors have now discovered that stress wave velocity in combination with certain log geometric parameters can be used to predict lumber warp with considerable accuracy. The geometric parameters can include but are not limited to such log defects as sweep or cross section irregularity. Using a sample population of logs, a multivariate regression equation must first be determined to set up the relationship for each species and general geographic area where the trees are grown. A representative group of trees, generally at least about 10 and preferably 50 or more, are examined for stress wave velocity and geometric configuration. These trees are then sawn conventionally except that the lumber from each tree is marked so that its source tree is known. After drying and subsequent finishing operations any observed warp of the lumber is measured. This warp can then be related to the earlier measured properties of the tree.

Inclusion of stress wave velocity with even a single geometric parameter in the regression equation has almost doubled the predictability accuracy compared with stress wave velocity standing alone. For prediction of crook, one such geometric parameter is the average difference in center locations of adjacent cross sections relative to the longitudinal reference line. This is a measurement indicative of log sweep. Inclusion of additional geometric measurements further increases the predictability. Similarly, measurements related to log eccentricity or other cross sectional irregularity when combined with stress wave velocity, are predictive of bow in the sawn lumber.

It is an object of the present invention to provide a method that has reliable predictive power indicating which logs might produce warp prone lumber.

It is a further object to provide a method that uses stress wave velocity and log geometric parameters in combination to indicate logs that might produce warp-prone lumber.

It is another object to create a multivariate regression equation with log stress wave velocity and log geometric parameters as independent variables predictive of lumber warp.

It is yet an object to use log geometric parameters indicating sweep and cross sectional eccentricity in combination with stress wave velocity as lumber warp predictors.

These and many other objects will become readily apparent to those skilled in the art upon reading the following detailed description taken in conjunction with the drawings.

BRIEF DESCRIPTION OF THE DRAWINGS

FIGS. 7–11 show various types of warp that can occur in sawn lumber.

FIG. 14 illustrates a log with sweep entering a pair of side-by-side primary breakdown saws.

FIG. 15 shows the subsequent sawing pattern of the cant generated by the saws in FIG. 8.

DETAILED DESCRIPTION OF THE PREFERRED EMBODIMENTS

Figure 1:
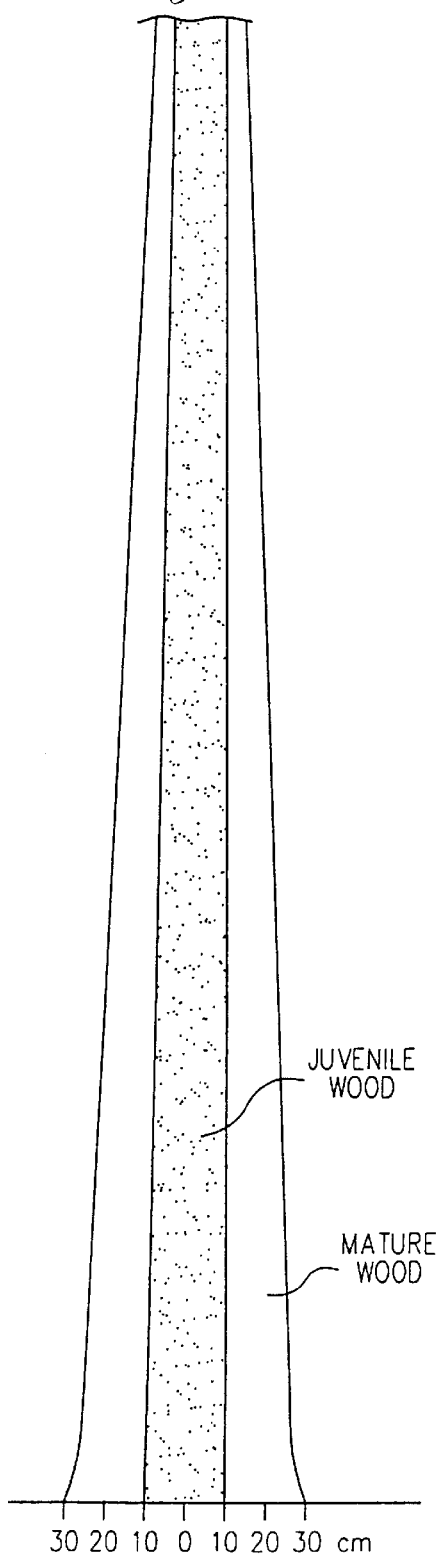
FIG. 1 is an idealized illustration showing the location of juvenile wood in the stem of a pine tree approximately 20 m high and of 35 years age.

The trunk of a conifer may be visualized as a stack of hollow cones of ever increasing length and base diameter and ever decreasing included angle. Each cone will represent an individual year's growth and is indicated in cross section by an annual growth ring. As shown in FIG. 1, wood having juvenile characteristics can be represented as a cylinder located along the entire longitudinal axis of the tree, this cylinder being about 10–15 growth rings wide. It is apparent that the upper (and younger) portion of the tree will have a greater ratio of juvenile wood to wood having mature characteristics. The so-called "heart wood" that forms later during the tree's development does not alter the juvenile characteristics of the interior fibers.

The ideal log coming into a sawmill would be in the form of a true cylinder. This ideal form is rarely seen since most logs have at least some taper. Tapered logs can be described as frustroconical in form. Yet even this geometric form, in which cross sections are uniformly circular and the longitudinal axis centered and linear, is rarely seen. Sweep is a typical deviation from the ideal form. This is defined as curvature or deviation from linearity of the longitudinal axis. The axis may have simple or compound curvature. Typical logs also frequently have at least some deviation from circular cross sections. This is usually in the form of ellipticity but the cross section may be considerably more complex and irregular, at least along part of the log.

Figure 2:
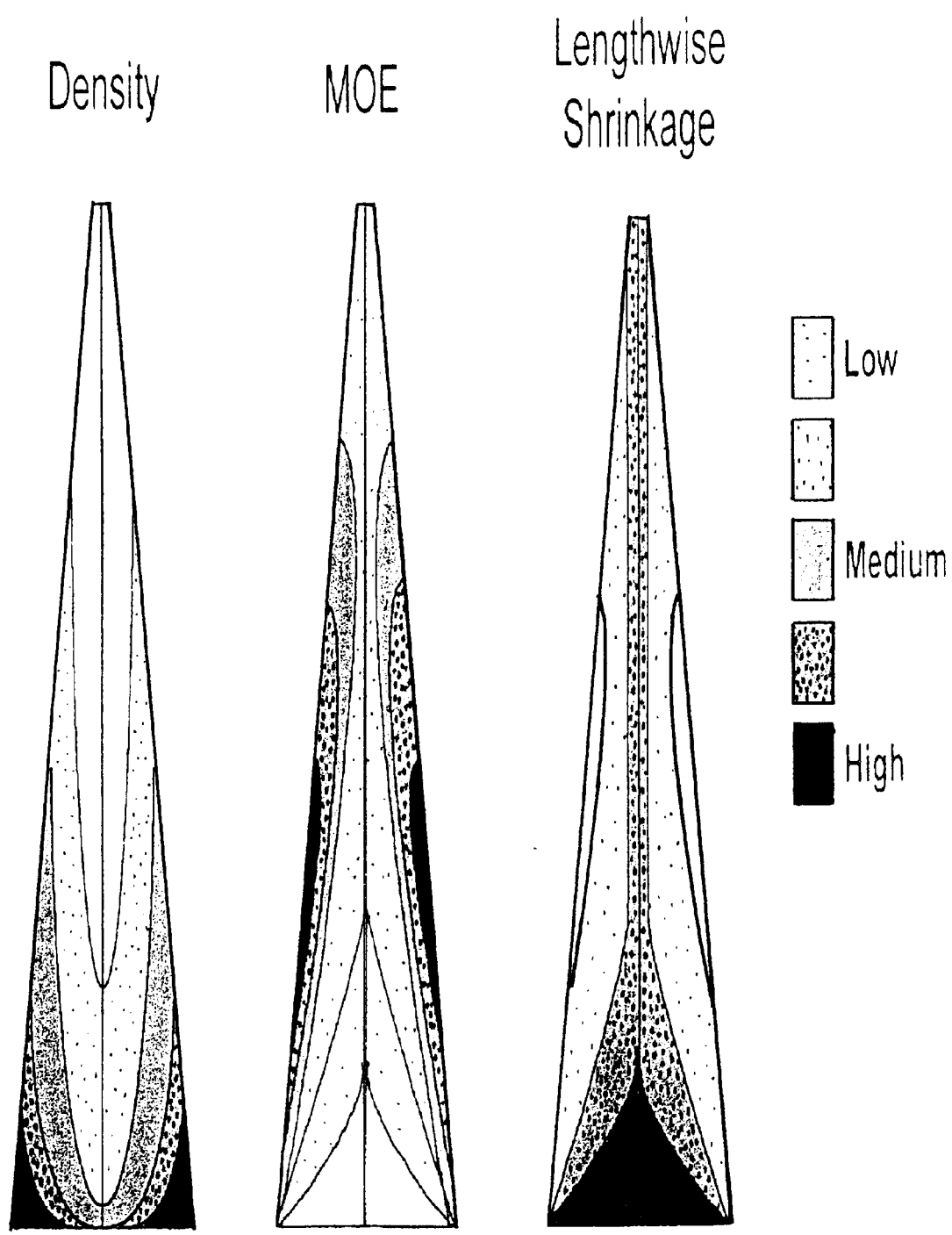
FIG. 2 shows distribution of density, modulus of elasticity, and lengthwise shrinkage in a 20 year old southern pine tree.

FIG. 2 shows a plot of the general patterns of within-tree distribution of density, modulus of elasticity, and lengthwise shrinkage measured on a sample of 20 year old plantation grown southern pine trees. The density pattern somewhat resembles the shape of a tulip blossom or wine glass. High density wood surrounds the base of the tree. There is a low MOE, high shrinkage core at the base of the tree and a high MOE sheath or collar located about 2.5–7.5 m above the base. Shrinkage is high throughout the entire central portion of the tree.

Figure 3:
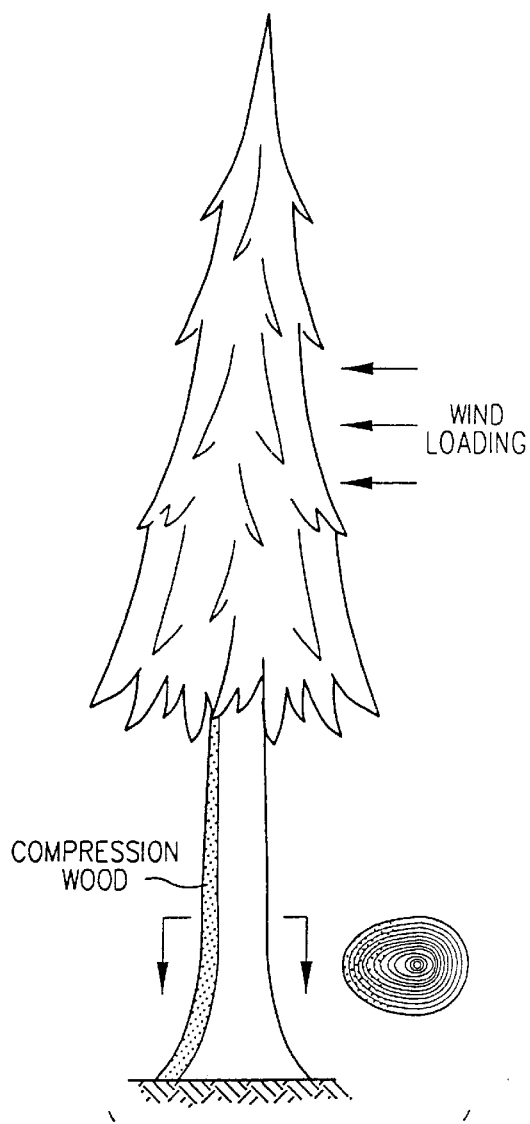
FIG. 3 illustrates the formation of compression wood as a reaction to prevailing winds.

The stresses that must be balanced at the growing cambium layer of a tree are the result of combined compressive and bending loads due to gravity and wind. The axiom of uniform stress teaches that a tree distributes its growth around its annual rings in a pattern that is seeking to achieve a uniform stress distribution (C. Mattheck, *Design in Nature: Learning from Trees*, Springer-Verlag, Berlin (1998)) (see also FIGS. 3–6 of the present application). In coniferous trees, as seen in FIG. 3, this results in a biasing of each annual growth ring so that the greatest ring width occurs along the radius where the largest bending (compression) load exists. Wood is known to be stronger in tension than it is in compression. This further biases distribution of growth in coniferous species to zones where compressive stresses are highest. It is also known that microfibril angle of tracheids is proportional to the average compressive loading in the vicinity of the fiber at the time the fiber is formed (see Boyd, J. D. and R. C. Foster. Tracheid anatomy changes as responses to changing structural requirements of the tree. *Wood Science and Technology* 8: 91–105 (1974)). Since microfibril angle is known to be proportional to lengthwise shrinkage it would be expected that lengthwise shrinkage would also be proportional to the average compressive loading in the vicinity of the fiber at the time of its formation. One may assume that if the width of an individual growth ring varies significantly around the tree, shrinkage gradients will exist within that ring. It would then be expected that if radial shrinkage gradients exist within a log, lumber cut from that portion of the log would be prone to warp. Stated differently, whenever a tree is growing in such a way that the width of individual rings varies significantly around the tree, shrinkage gradients exist within that ring and lumber sawn from the vicinity of these gradients will be prone to warp. It may be assumed by the same reasoning that logs having a uniform circular cross section and uniform ring width would produce lumber less prone to warp than lumber cut from logs having a non-circular cross section or non-linear longitudinal axis.

Figure 4:
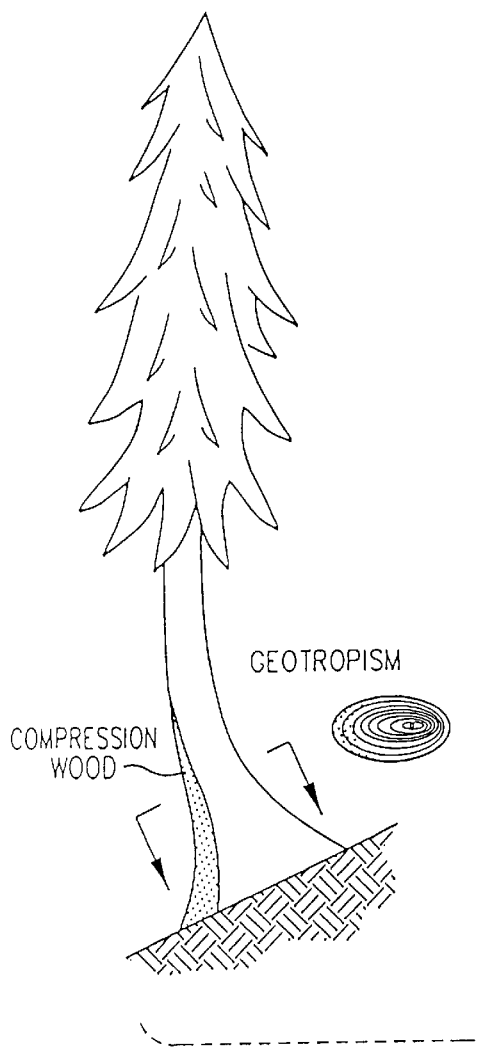
FIG. 4 illustrates the formation of sweep and compression wood in a tree due to geotropism.
Figure 5:
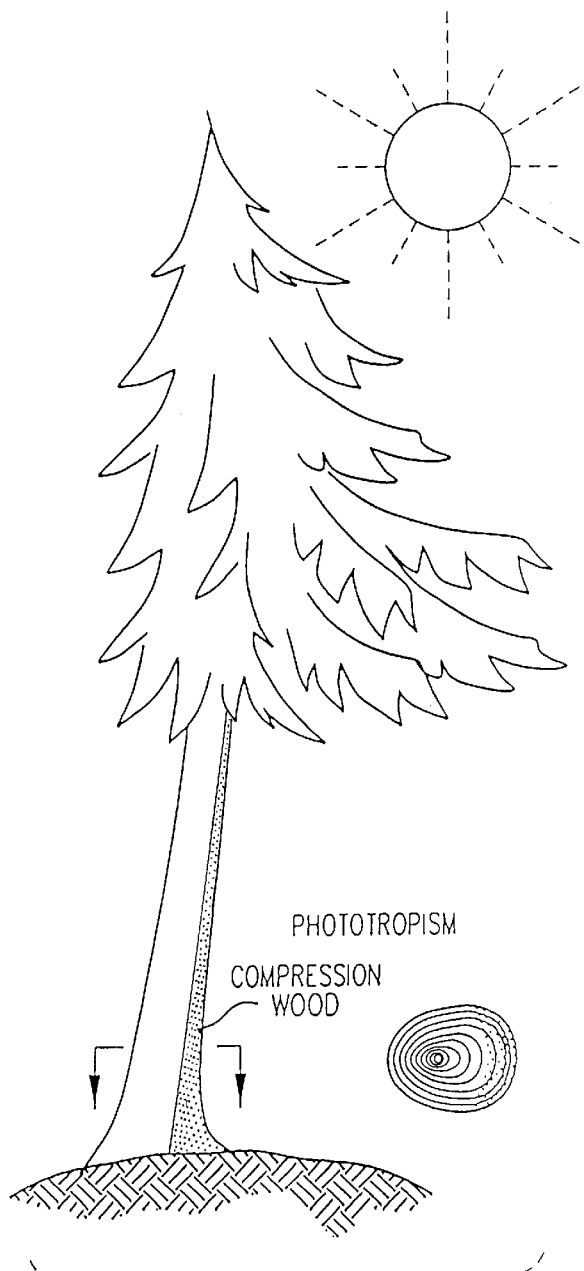
FIG. 5 similarly shows formation of compression wood and stem ellipticity in a tree unbalanced by phototropism.
Figure 6:
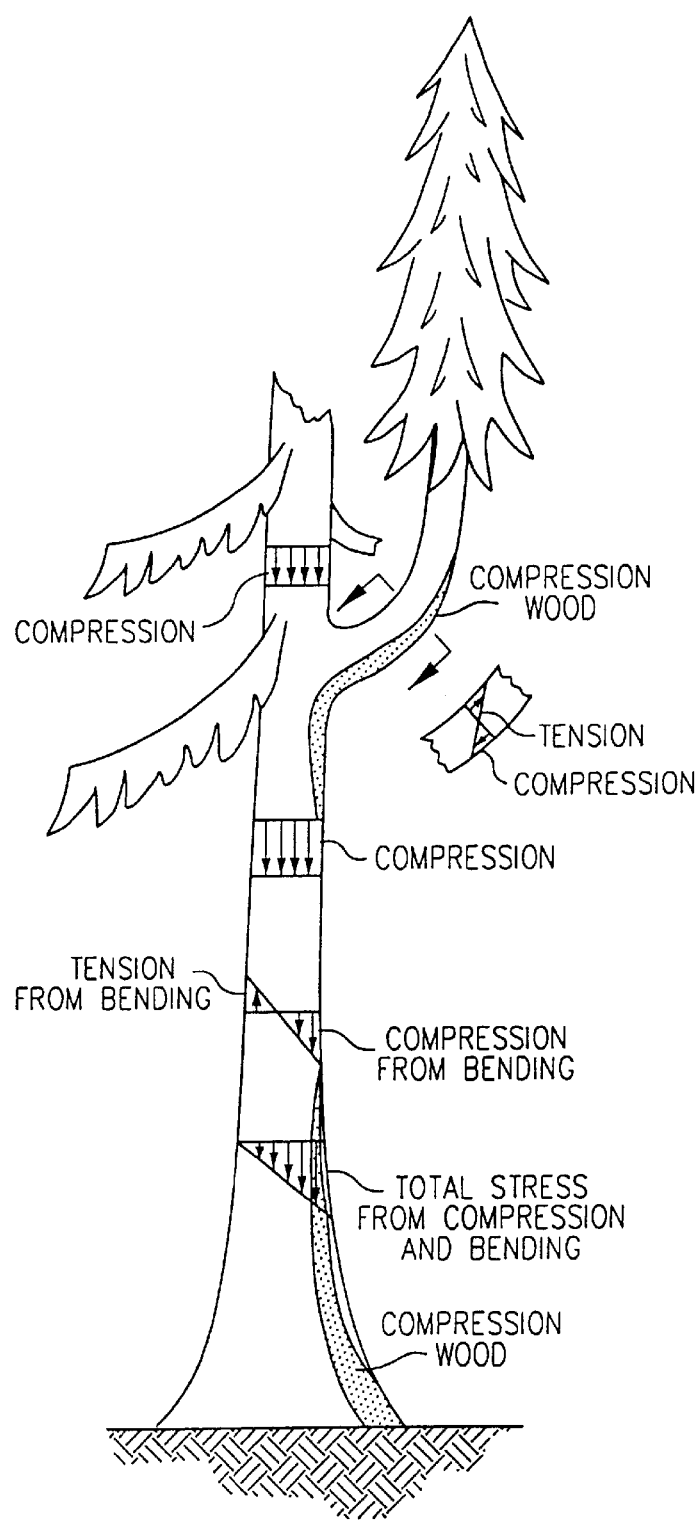
FIG. 6 illustrates compression wood formation and stresses resulting from geotropism acting on a tree developing a new top due to earlier damage in a windstorm.

Trees possess two important growth-regulating mechanisms which affect wood formation and placement. Geotropism tends to direct trees to grow erect against gravitational pull (FIGS. 4 and FIG. 6). Phototropism causes trees to locate branches so as to receive maximum light (FIG. 5). This figure illustrates a tree that might have been growing at the edge of a clearing with the branches being heavily one-sided as they sought light outside the forest canopy. Both of these mechanisms tend to override the axiom of uniform stress. This results in the formation of compression wood on the side of a tree 180° from the direction toward which the tree is attempting to reorient. Both mechanisms, if left uncorrected as the tree forms new wood, would cause mechanical unbalance that would seriously weaken the tree. With conifers, growth in response to stresses induced by phototropism or geotropism results in formation of additional compression wood to balance the induced stresses (see FIG. 6, redrawn from Mattheck 1997). In the illustration of FIG. 6 a tree has lost its top, perhaps in a windstorm, and an upper branch has taken over to become the new apical portion. The resultant stress is the additive compressive stress from the weight of the tree and the bending stress from the new off-axis upper portion. Once geotropic and phototropic responses have begun to shift the tree's canopy away from its neutral axis, the axiom of uniform stress will likely result in further wood property gradients around subsequent annual rings.

As was noted earlier, sweep is a condition of non-linearity in a tree stem; e.g., as seen in FIG. 4. It is interesting that a phototropic or geotropic response resulting in compression wood formation on the convex side of conifers can also develop a corresponding high microfibril angle on the opposite (concave) side of the same cross section. This is dictated by the axiom of uniform stress. It is also important that a tree with sweep tends to "fill in" the concave side to mask the sweep. One would expect that logs from the portion of trees that have (or have earlier had) sweep would produce warp prone lumber. Similarly, logs that have been straight throughout their growth would tend to produce more warp stable lumber. The present inventors have indeed found this to be the case.

It is important to note that the width increases on annual growth rings where wood having a high microfibril angle is formed. Thus, if a tree's ring pattern could be observed one could infer where the zones of high longitudinal shrinkage are located by looking for those locations where individual growth rings widen. Unfortunately, this is not as yet commercially practical. Alternatively, location of these high shrinkage zones might be inferred by analyzing cross sectional shapes. From the previous discussion, one could assume that wherever a tree's cross section deviates from a smooth circular shape, longitudinal shrinkage gradients would exist in that area and lumber sawn from that location will be prone to warp. Thus, not just sweep but over all log geometry as well are factors that should be considered in predicting warp proneness.

Warp in lumber assumes several forms that may be present singly or in combination. As seen in FIGS. 7 and 8, crook and bow are the result of differential longitudinal shrinkage in various portions of sawn lumber. One must differentiate between "longitudinal shrinkage" which is measured parallel to the fiber direction, and "lengthwise shrinkage" which is measured parallel to the longitudinal axis of the board (FIG. 9). These may or may not be the same. Cup, shown in FIG. 10, is principally the result of variations in tangential shrinkage which tends to increase as one moves outward from the pith. Twist, as illustrated in FIG. 11, is normally the result of spiral grain in the log from which the lumber was sawn.

Figure 12:
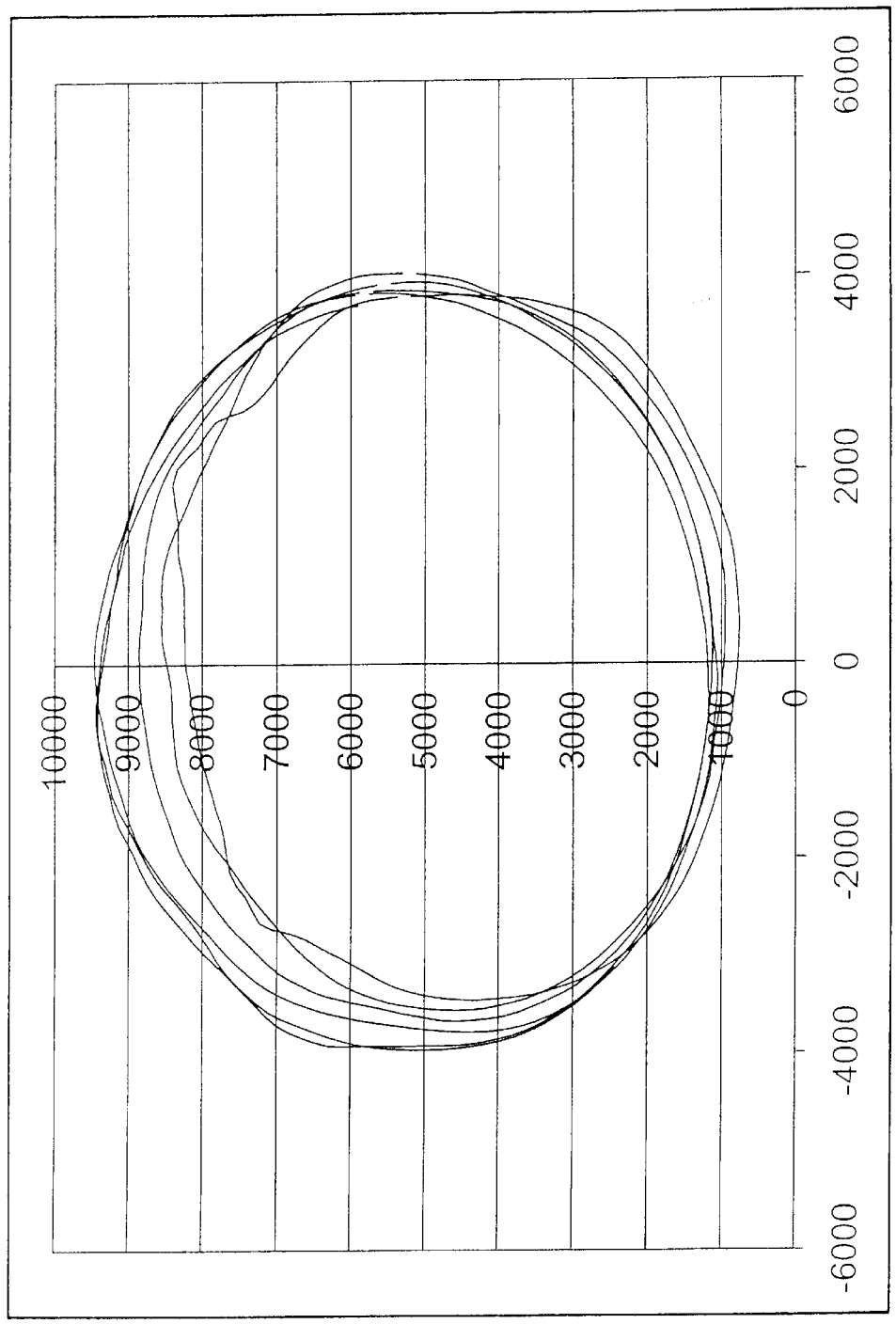
FIGS. 12 and 13 show actual superposed circumferential scans along the lengths of two logs having different geometric configurations.
Figure 13:
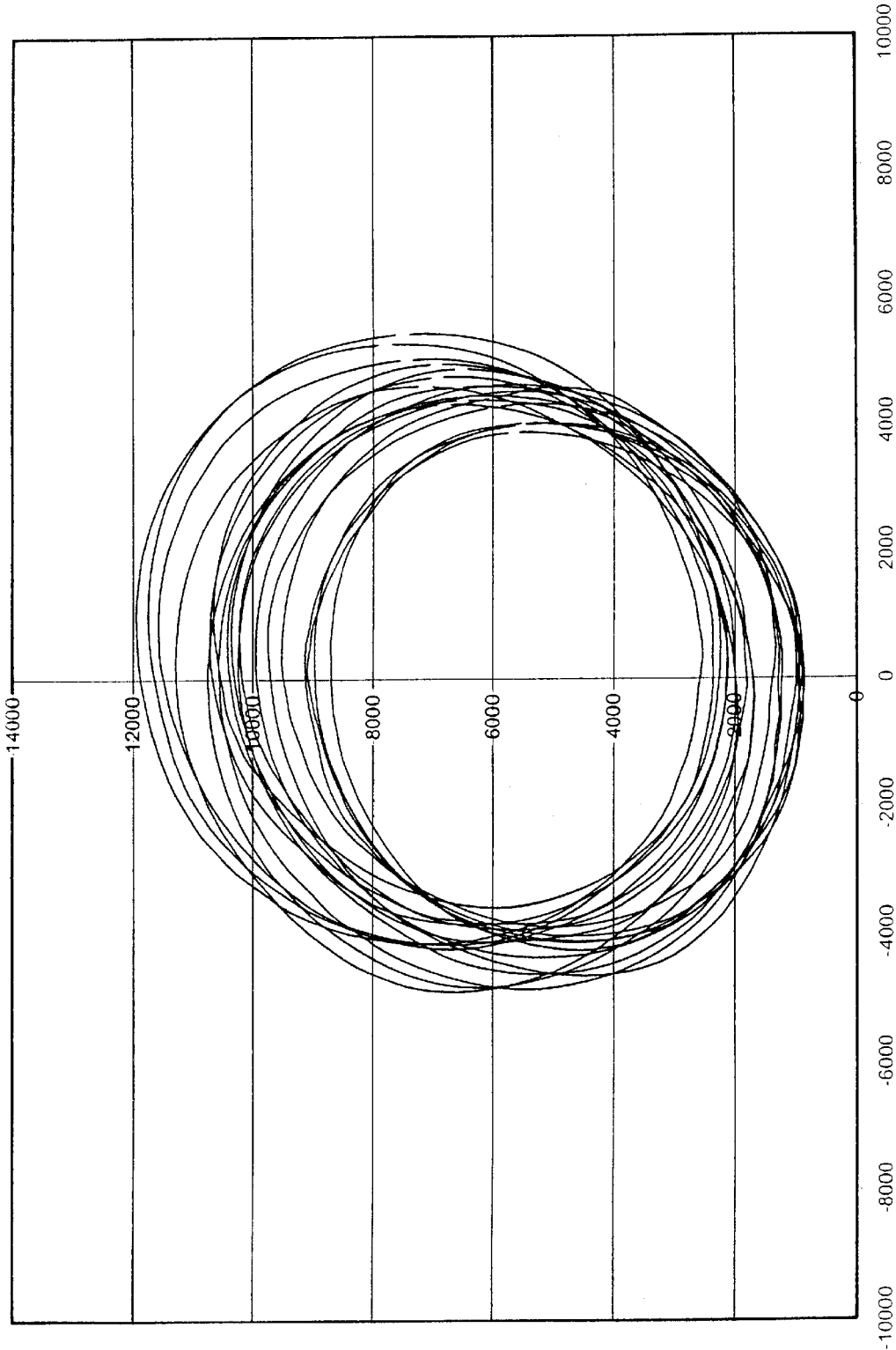

The days in which a head sawyer made real time decisions as to how a log should be optimally cut have largely passed with the near disappearance of the huge old growth logs from the nations forests. Automation in sawmilling is now a fact of life for most but the smallest mills. The smaller logs now grown in tree farms must be processed at dazzling rates in order for mills to be competitive. Scanners and computers now make most of the decisions formerly made by the head sawyer. Logs are now typically scanned for size and geometric configuration as they approach the head saw or primary processing center. A typical scanner will make multiple determinations of the log circumference at short intervals along the length. These measurements will denote log diameter, length, and taper, as well as longitudinal sweep and any eccentricity. FIG. 12 shows six superposed scans of a log having little sweep and a generally round, although irregular, cross section. FIG. 13 illustrates eighteen superposed scans along a log having a somewhat elliptical cross section and significant sweep. Vertical and horizontal scales differ somewhat and distort the apparent cross sections. It can be presumed that the y axis is vertical and the x axis horizontal. The scanners are generally based on a battery of laser distance measuring cameras that perform the task without log rotation. Information from the scanners is entered into a computer programmed to automatically determine the best orientation of the log as it enters the primary breakdown saw. The log will then be automatically rotated through the desired angle relative to its position when scanned. The computer will also set the saws for the initial cuts to get the maximum lumber value from the log.

Normally the optimum orientation of a log with sweep moving into the primary breakdown saws is with "horns up" or "horns down". This means that the plane of any sweep should be oriented parallel to the saws, usually vertically, in order to obtain maximum lumber yield. FIG. 14 illustrates a log 2 with sweep being carried horns down on a sharp chain 4 into a pair of band saws 6 for primary breakdown. Spacing of the saws has been adjusted by the computer output to take off two slabs 8, each of which will yield a side board 10. As seen in FIG. 15 the resulting cant 12 may be further directed into a gang saw where boards 14, 16, and 18 will be cut. Boards 14 and 16 will then be resawn and edged to their nominal rectangular cross section.

By cutting the log either horns up or horns down the resulting cant will be flat sided but retain the original sweep. This may be sawn conventionally in which the best rectangular parallelepiped is cut. The sweep will thus be lost as waste or pulp chips. New sawing systems are now widely used that follow the sweep curvature as the cants are further processed into lumber. The resulting boards initially retain this curvature but are later flattened during kiln drying. A significantly improved lumber yield is achieved with so-called around-the-curve sawing.

Figure 16:
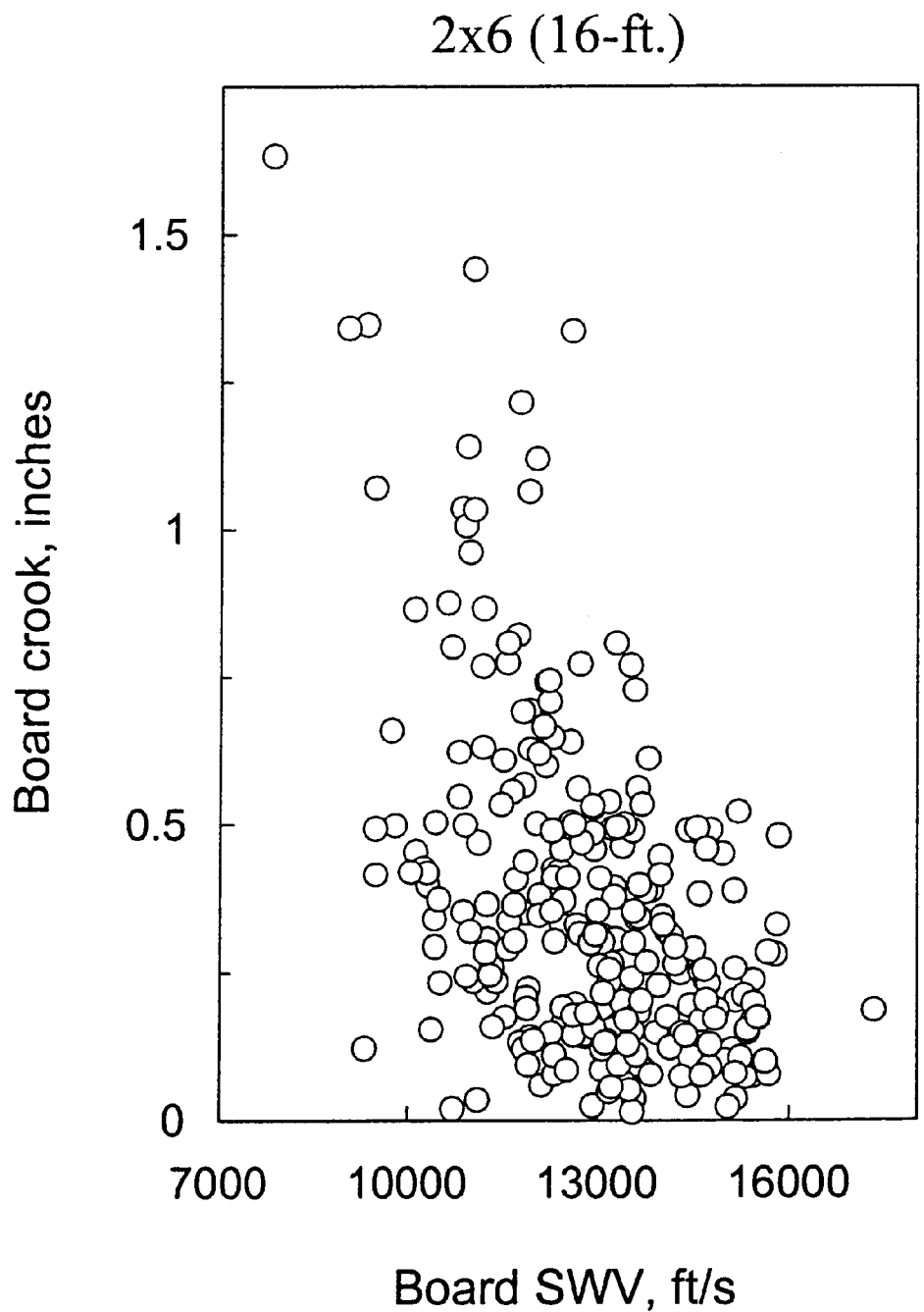
FIG. 16 is a plot of sound wave velocity plotted against crook for 16 ft long nominal 2×6 inch southern pine plantation wood lumber.
Figure 17:
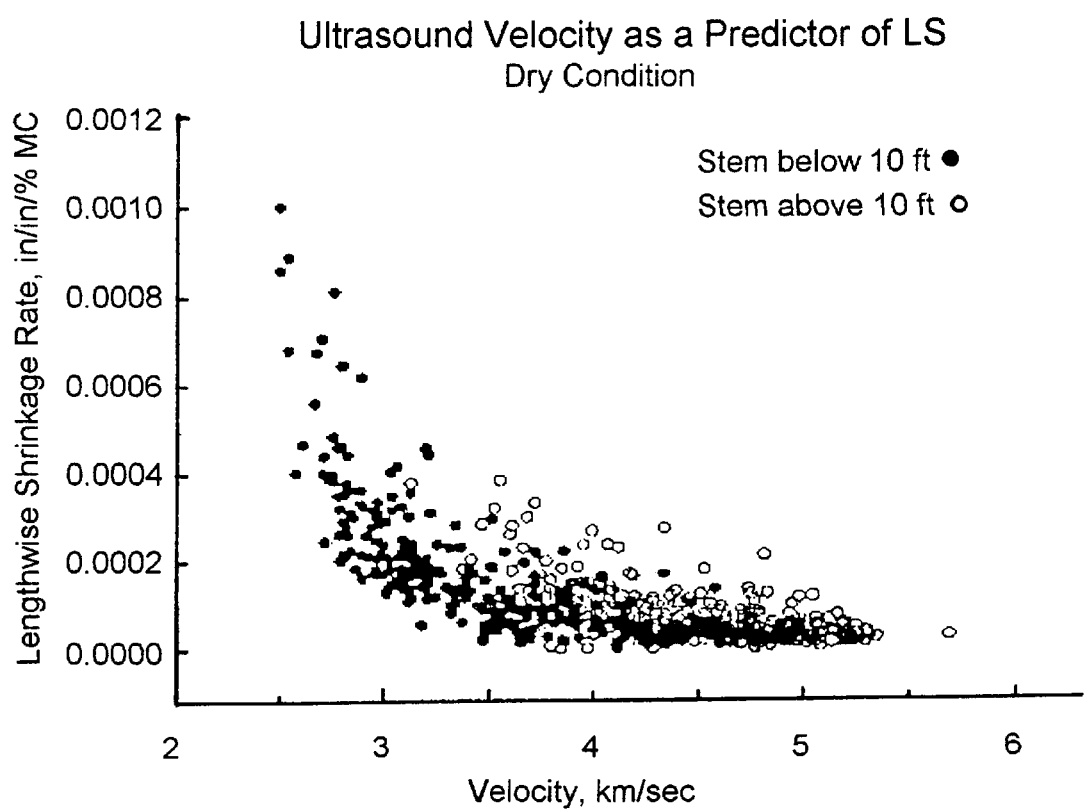
FIG. 17 shows a plot of lengthwise shrinkage of lumber againts stress wave velocity.

It has been noted that warp prone lumber tends to have relatively lower sound wave propagation rates and accompanying low stiffness. FIG. 16 shows a plot of stress wave velocity plotted against crook for 16 ft long nominal 2×6 inch southern pine plantation wood lumber. Stress wave velocity was measured using a Sylvatest Duo instrument, available from CBS-CBT, Lausanne, Switzerland. This employs a probe at each end of the piece being measured. There is a rather poor trend seen to greater crook at lower stress wave velocity for individual pieces of lumber. One possible explanation is that lengthwise shrinkage is much more variable in wood having low stress wave velocity. FIG. 17 shows the plot of lengthwise shrinkage vs. stress wave velocity for a large data base. The curve is generally hyperbolic in form and the trend to high shrinkage at low stress wave velocity is very clear from this plot. However, accurate crook and bow prediction of individual lumber pieces requires a detailed knowledge of lengthwise shrinkage patterns across and along the length. These shrinkage patterns can be inferred by measuring acoustic velocity patterns across and along the surface of the individual piece, as shown in published PCT application WO 00/12230. Given the difficulty of predicting the warp propensity of individual pieces of lumber one would expect even greater difficulty in predicting the warp expected of lumber not yet sawn from whole logs. Indeed, as seen in FIG. 16, attempts to correlate lumber warp with average stress wave velocity have been poor. In similar fashion, as seen in the earlier cited article to Wagner and Taylor, attempts to correlate lumber warp with log sweep has shown only limited promise.

While it appears that lumber warp such as crook or bow was related in some way to stress wave velocity there apparently were other important factors unaccounted for. Similarly, tree geometry has by itself been a relatively poor predictor of lumber warp propensity. This has been the case even though asymmetry in cross-section or non-linearity of the longitudinal axis would suggest the presence of comression wood known to have different shrikage characteristics that wokd affect lumber warp. The present invention shows that combining measurements of stress wave velocity with log geometry measurements is much more useful in predicting warp propensity of lumber cut from the logs than any single measurement previously investigated.

A sawing study was conducted in which 80 loblolly pine plantation trees from three Arkansas stands were harvested, bucked into two 16 foot (4.88 m) lengths and sawn into nominal 2 inch dimension lumber in nominal 4–12 inch widths. The three stands ranged in age from 20 to 24 years old and the trees averaged 10.5 inches (267 mm) in diameter at breast height. All processed lumber was coded to relate to the log from which it was sawn. The test lumber was kiln dried and graded according to normal mill practice. After grading several test sizes were retrieved for warp evaluation. These sizes included nominal 2×4s in 12 and 16 foot lengths, 2×6s in 14 and 16 foot lengths, and 2×8s in 12 and 16 foot lengths. The data set included trees that yielded at least three pieces of lumber. Warp measurements were made on these pieces using methods detailed by the Southern Pine Inspection Bureau lumber grading standards. Average warp of all pieces cut from an individual tree was then computed. Eight measurements potentially correlated with lumber warp were taken on each test tree and log before it entered the sawmill to be processed into lumber.

Stress wave velocity was measured using two instruments. A portable hand held instrument available from FAKOPP Enterprises, Agfalva, Hungary, was used to obtain breast height measurements on the trees before they were felled. Average stress wave time of three measurements (0°,+20°, and −20° from vertical) were made with the two probes placed between 0.5 m and 1.5 m apart. This same instrument was also used to measure stress wave velocity on the felled trees using probes set in each end of the logs. An additional stress wave measurement was made on the felled logs using the resonance method described by Snyder et al. in U.S. Pat. No. 6,026, 689. In this method the impacting device and receiving transducer were both located at one end of the log. Measurements taken were as follows:

1. Average stress wave time at breast height of tree, $\mu$sec—Fakopp method.
2. Stress wave velocity over full length of first 16 ft log (ft/sec)—Fakopp method.
3. Stress wave velocity over full length of second 16 ft log (ft/sec)—Fakopp method.
4. Average stress wave velocity of first and second logs (ft/sec)—Fakopp method.
5. Stress wave velocity of first log (ft/sec)—Snyder et al. resonance method.
6. Breast height diameter outside bark (in).
7. Average diameter at large end of log.
8. Taper over 32 ft length measured inside bark (in/ft).
9. Number of annual rings in outer 1.5 inches (38 mm)

Taper was determined by subtracting the diameter at the upper end from the butt end diameter and dividing by log length. The original 32 ft logs were then cut into 16 ft lengths for the sawmill.

As each log approached the primary breakdown center geometric data were generated by the Perceptron Log Optimizer software using four TriCam laser scanners. This equipment, manufactured by Perceptron Forest Products Division, Atlanta Ga., is typical of many of the scanners used in sawmills. Scanners used at this location will normally determine the best log orientation entering the saw and the optimum saw settings. In the present test the scanners measured x-y coordinates at about 100 points around the circumference of the log at each 1 ft (305 mm) increment along the log (refer to FIGS. 12 and 13 as examples). The x values and y values of each circumferential scan were averaged to determine a center point location. A longitudinal line is chosen as a reference location. Sixteen additional measurements potentially correlating to lumber warp were derived from the scanning data.

A. Major axis sweep (in).
B. Minor axis sweep (in).
C. Combined sweep (in).
D. Maximum x change (in).
E. Average x change (in).
F. Standard deviation of x change.
G. Maximum y change (in).
H. Average y change (in).
I. Standard deviation of y change.
J. Average major diameter
K. Standard
M. Standard deviation of minor diameters
N. Maximum eccentricity (in).
O. Average eccentricity (in).
P. Standard deviation of eccentricity.

Sweep typically will predominantly lie in a single plane but may be more complex. The scanner was programmed to determine the predominant plane and a minor plane of sweep, if one existed. Sweep in the predominant plane was designated the major axis sweep. Combined sweep was determined by taking the square root of the sum of the squares of the major axis and minor axis sweep measurements.

Maximum x change was calculated by taking the largest difference between the values of the x center locations of adjacent cross sections, relative to the reference line. Maximum y change was similarly calculated. Averages and standard deviations were determined using data from all sections. These measurements again are indicative of sweep. The x and y values were calculated on the logs in the position scanned. The major sweep plane of the log would normally be about horizontal and minor sweep nominally vertical when scanned. The opposite situation would prevail when the log is sawn since the log would usually be rotated through an appropriate angle so that the plane of the major sweep would be vertical. As will be seen below, the average change of the y center positions was an important predictor of lumber crook. This supports a finding that it is the compound curvature (curvature typically about 90° from the major sweep plane) that influences lumber crook when the log is cut with the major sweep axis lying in the vertical plane. This obviously also assumes that the saws are vertically oriented. The values reported in Table 1 that follows were calculated on the basis of the log as scanned and were not (computer) rotated to the position in which the log might be sawn. Were the values based on center positions of the log as it would be rotated to sawing position, the average x center locations would become the more important predictor.

Major diameter is the largest diameter and the minor diameter the smallest diameter computed at each cross section. Eccentricity is computed as the square root of the squared major diameter minus the square of the minor diameter for each scanned section. The average eccentricity is determined from all cross sections and the maximum from the greatest eccentricity measured in a single section.

Each of the variables studied was analyzed using a multiple linear regression program to see which factors singly or in combination, if any, correlated with measured lumber warp. Many such statistical analysis programs are readily available as commercial products or in the public domain. The second group of variables (A-P scanner determined variables) were studied for just the first 16 foot log. Tables 1 and 2 summarize the key results of this analysis for crook and bow. These tables display the sets of variables that were (a) significantly correlated with warp ($p<0.05$) and (b) explained at least 9% of the warp variability ($R^2>0.09$). In all tables following the x and y values are unrotated. Otherwise stated, they are in the position as scanned relative to the reference line.

TABLE 1

Variables Correlating with Lumber Crook

| Variable Number | Variable | $R^2$ | P Value |
|---|---|---|---|
| 1 | Breast height stress wave average | 0.255 | 2.03E-06 |
| H | Average y change | 0.25 | 3.10E-06 |
| 4 | Stress wave avg. first and second logs | 0.22 | 1.56E-05 |
| 8 | Taper (1–32 ft) | 0.216 | 1.61E-05 |
| 5 | Log 1 stress wave resonance method | 0.19 | 5.39E-05 |
| 2 | Stress wave average first log | 0.19 | 5.40E-05 |
| G | Maximum y change | 0.17 | 0.00016 |
| I | Standard deviation y change | 0.13 | 0.0014 |
| C | Combined sweep | 0.11 | 0.003 |
| K | Standard deviation major diameter | 0.11 | 0.003 |

It will be noted in the above table that variables 1, 2, 4, and 5 are measuring similar properties (stress wave velocity related) as are variables C, G, H, and I (sweep related).

TABLE 2

Variables Correlating with Lumber Bow

| Variable Number | Variable | $R^2$ | P Value |
|---|---|---|---|
| J | Average major diameter | 0.155 | 0.00033 |
| L | Average minor diameter | 0.147 | 0.00050 |
| 6 | Diameter at breast height | 0.138 | 0.00077 |
| 7 | Average diameter at butt end of first log | 0.119 | 0.00183 |
| 1 | Breast height stress wave average | 0.093 | 0.00636 |

None of the variables investigated showed significant correlation with twist. This was not unexpected since twist is primarily caused by spiral grain and not the shrinkage factors that affect crook and bow.

Figure 18:
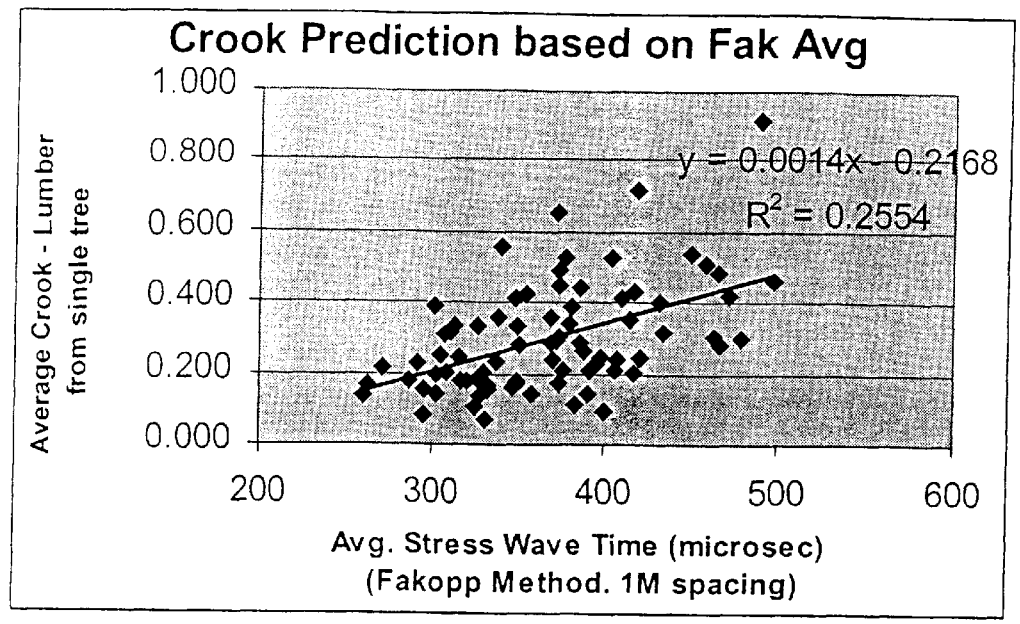
FIG. 18 is a plot of actual lumber crook against predicted crook based solely on stress wave velocity measured in logs from which the lumber was sawn.

A graph showing stress wave velocity alone, measured on the logs, plotted against measured lumber crook for the present data set is shown as FIG. 18. As can be readily seen, the point scatter is quite wide and correlation relatively poor.

Figure 19:
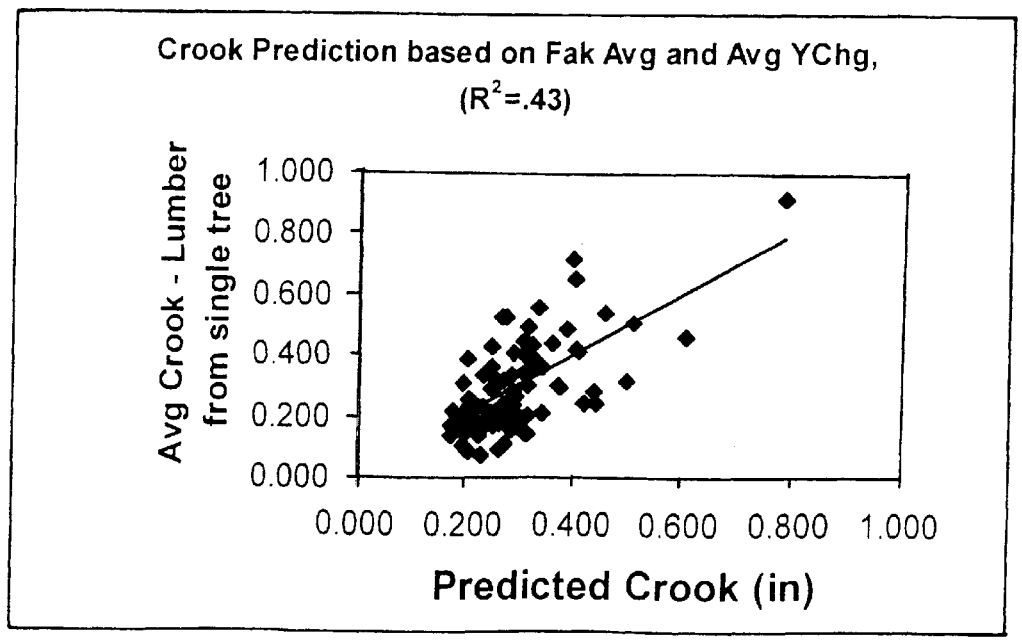
FIG. 19 is a plot similar to that of FIG. 18 in which both stress wave velocity and log y values of center points indicating sweep were used in predicting lumber crook.

Drawing from the list of variables in Table 1, two multivariate models were developed to predict the average lumber crook expected from an individual log. The simplest model used two variables and a better model used four variables and their products. The first used (1) stress wave time at breast height of the tree and (2) average y change, a measure of average curvature of the log. The better model used these and added (3) standard deviation of the major diameters of the log, and (4) standard deviation of y change, the latter variable again relating to log curvature. A plot using the first model is shown as FIG. 19. Point scatter has been greatly reduced. Adding average y change to stress wave time increased $R^2$ from 0.255 to 0.43, a very significant improvement in prediction of crook. Coefficients of the equation are shown in Table 3.

TABLE 3

Two Variable Crook Prediction Model

| Variable | Coefficient |
| --- | --- |
| Intercept | 0.223 |
| Average y change | −2.160 |
| Avg stress wave time at breast height | −0.00019 |
| Avg y change X Stress wave average | 0.0085 |

Figure 20:
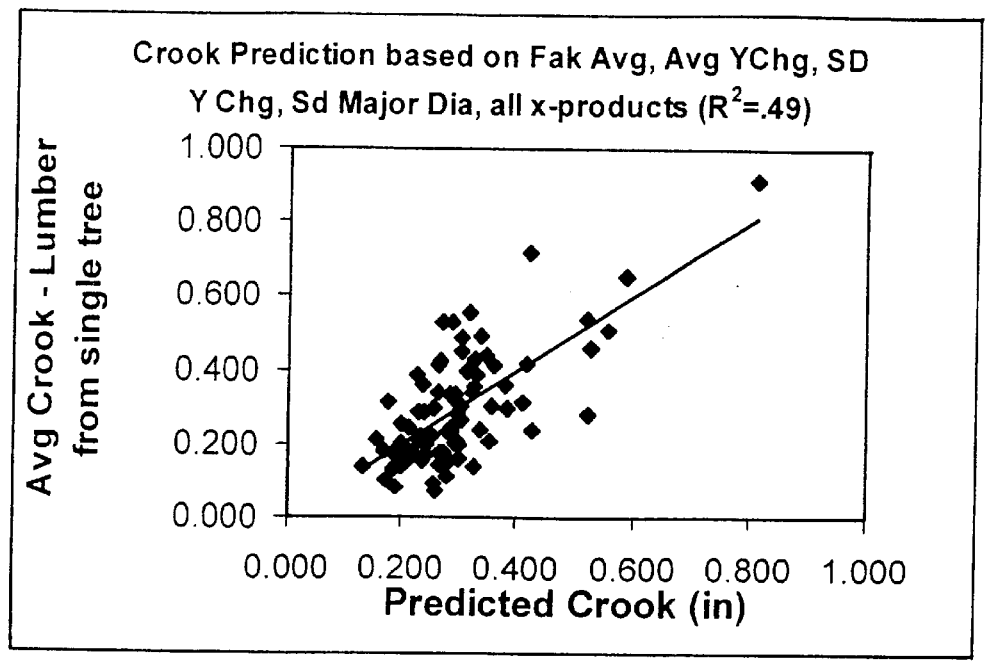
FIG. 20 is similar to FIG. 15 but with additional log geometric parameters added to the equation.

A better model which used the four variables is shown in Table 4 and plotted as FIG. 20.

TABLE 4

Four Variable Crook Prediction Model

| Variable | Coefficient |
| --- | --- |
| Intercept | 0.0224 |
| Average y change | −5.528 |
| Standard deviation y change | 7.300 |
| Standard deviation major diameter | −0.133 |
| Avg stress wave time at breast height | 0.00019 |
| Avg y change X S.D. y change | −6.531 |
| Avg y change X S.D. major diameter | 3.678 |
| Avg y change X Stress wave time | 0.0134 |
| S.D. y change X S.D. major diameter | −3.577 |
| S.D. y change X Stress wave time | −0.0104 |
| S.D. major diam X Stress wave time | 5.639E-05 |

By supplementing a stress wave velocity measurement with three geometric measurements the models accuracy in predicting crook was essentially doubled. $R^2$ was raised from 0.255 to 0.49. Data shown here were drawn from all widths and lengths of the lumber produced in the study.

Figure 21:
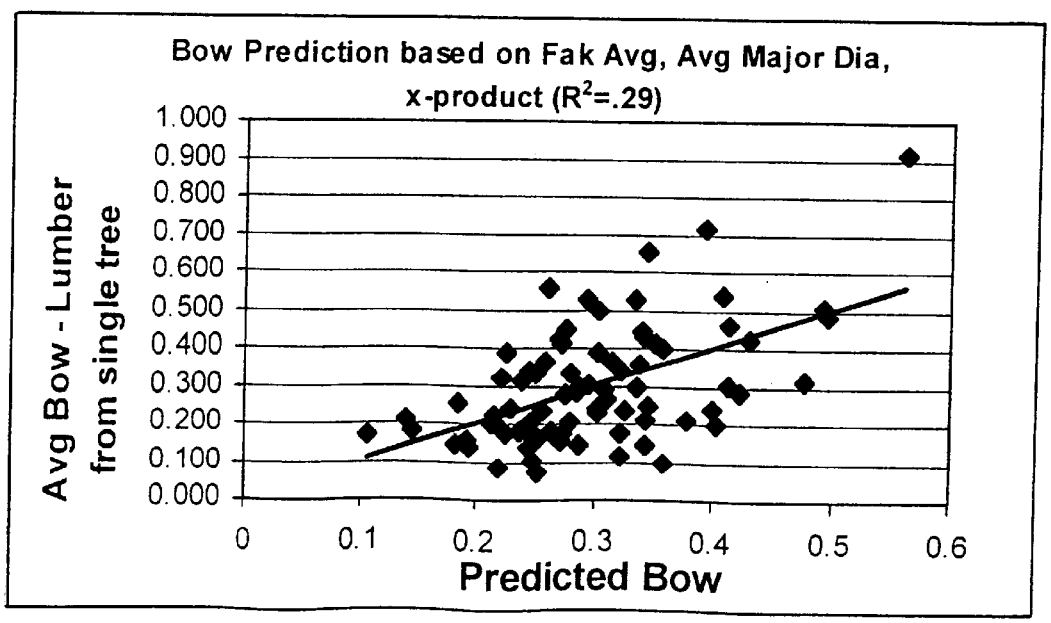
FIG. 21 is a plot showing relationship of bow to log geometry and stress wave velocity.

A similar multivariate model was developed to predict average lumber bow based on the variables studied. The best bow model used two variables and their product. These were (1) stress wave time at breast height, (2) the average major diameter of the first log, and their product. Overall bow was less predictable than crook. However, by supplementing the stress wave velocity measurement with a geometric analysis the models accuracy nearly tripled ($R^2$ was raised form 0.093 to 0.29). The resulting model is shown in Table 5 and plotted as FIG. 21.

TABLE 5

Bow Prediction Model

| Variable | Coefficient |
| --- | --- |
| Intercept | 1.0196 |
| Average major diameter | −0.1265 |
| Avg stress wave time at breast height | −0.0023 |
| Stress wave time X Avg Major diameter | 0.00038 |

In all of the correlations relating to warp the most useful stress wave velocity measurements were those made near the base of the tree It is readily apparent that a combination of stress wave analysis with log geometric data will greatly improve the predictability of crook or bow warp defects in lumber sawn from any given log. It will be evident to those skilled in the art that many variations can be made in the present invention that have not been specifically exemplified. These should be considered to be within the scope of the invention if encompassed within the following claims.

What is claimed is:

1. A method of estimating warp potential of lumber sawn from a log which comprises:

creating a stress wave in an individual log and measuring velocity of the stress wave;

measuring geometric configuration of the individual log to determine any deviations from cylindrical form, the geometric measurement or measurements being selected from those indicating any departure from axial linearity and those indicating any departure from circularity of cross section; and using the combined stress wave velocity and geometric configuration data to estimate warp potential.

2. The method of claim 1 in which the geometric measurements indicate departure from log longitudinal axis linearity.

3. The method of claim 1 in which the geometric measurements indicate departure from circularity in log cross section.

4. The method of claim 1 in which the geometric measurements include both departure from longitudinal axis linearity and cross section lack of circularity.

5. The method of claim 1 in which the log geometric configuration is determined by multiple scans to establish a plurality of circumferential configurations along the log length, each configuration being determined by measurement of multiple points around the log circumference, the scans being made orthogonal to a longitudinal reference line generally parallel to the log, the circumferential configurations being indicative of the log cross sections and their displacement from the reference line at the scan location.

6. The method of claim 5 in which stress wave velocity and at least measurements indicating departure from log longitudinal axis linearity are included as independent variables in a multivariate regression equation predicting lumber warp.

7. The method of claim 5 in which stress wave velocity and at least measurements indicating departure from circularity of cross section are included as independent variables in a multivariate regression equation predicting lumber warp.

8. The method of claim 5 in which stress wave velocity and measures indicating both departure from log longitudinal axis linearity and departure from circularity of cross section are included as independent variables in a multivariate regression equation predicting lumber warp.

9. The method of claim 1 in which the warp property predicted is crook.

10. The method of claim 1 in which the warp property predicted is bow.

11. A method of estimating warp potential of lumber sawn from a log which comprises:

sampling a representative group of logs of a common species and establishing a multivariate regression equation by correlating stress wave velocity and at least one geometric measurement of the logs with observed warp of lumber milled from the representative group of logs, the geometric measurement or measurements indicating deviations from a true cylindrical log form;

creating a stress wave in an individual log chosen from outside the representative group and measuring velocity of the stress wave;

measuring geometric configuration of the individual log to determine any deviations from cylindrical form; and entering the stress wave velocity and at least one geometric measurement into the regression equation to predict warp propensity of lumber that might be sawn from the individual log, the geometric measurement or measurements being selected from those indicating any departure from axial linearity and those indicating any departure from circularity of cross section.

12. The method of claim 11 in which the geometric measurements indicate departure from log longitudinal axis linearity.

13. The method of claim 11 in which the geometric indicate departure from circularity in log cross section.

14. The method of claim 11 in which the geometric measurements include both departure from longitudinal axis linearity and cross section lack of circularity.

15. The method of claim 11 in which the log geometric configuration is determined by multiple scans to establish a plurality of circumferential configurations along the log length, each configuration being determined by measurement of multiple points around the log circumference, the scans being made orthogonal to a longitudinal reference line generally parallel to the log, the circumferential configurations being indicative of the log cross sections and their displacement from the reference line at the scan location.

16. The method of claim 15 in which the points determining the circumferential configurations defining the cross sections are projected relative to a pair of mutually orthogonal axes, arbitrarily called the x and y axes, and the average x and y values are determined to indicate a centerpoint location relative to the longitudinal reference line for each individual circumferential configuration.

17. The method of claim 16 in which the longitudinal reference line is arbitrarily assigned as a z axis, the circumferential configurations defining the cross sections are placed in their proper relation and sequential location relative to the z axis, and displacement of the center points from the z axis are determined in order to estimate major and minor sweep axes of the log.

18. The method of claim 16 in which the average changes of the x and y center location coordinates are determined by calculating the differences between all adjacent cross section center point locations along the log length and averaging the values.

19. The method of claim 16 in which the maximum differences in the x and y center location coordinates between adjacent cross sections are determined.

20. The method of claim 15 in which the major and minor diameters of each cross section are determined as a measure of eccentricity.

21. The method of claim 11 in which the wrap property predicted is crook.

22. The method of claim 21 in which stress wave velocity and at least measurements indicating sweep are included as independent variables in the multivariate regression equation predicting lumber crook.

23. The method of claim 22 in which measures indicating log eccentricity are included with measurements indicating sweep as independent variables in the multivariate regression equation predicting lumber crook.

24. The method of claim 21 in which stress wave velocity and at least average change of the y center coordinates as scanned are included as independent variables in the multivariate regression equation predicting lumber crook.

25. The method of claim 22 which further includes the standard deviation of the y center coordinate locations as scanned and the standard deviation of the major diameters of the cross sections as independent variables in the multivariate regression equation predicting lumber crook.

26. The method of claim 11 in which the warp property predicted is bow.

27. The method of claim 26 in which stress wave velocity and at least measurements indicating major and minor diameters are included as independent variables in the multivariate regression equation predicting lumber bow.

28. The method of claim 11 in which the log stress wave measurement is made adjacent the end of the log nearest the base of the tree.

* * * * *